United States Patent [19]

Sugo

[11] Patent Number: 5,364,638
[45] Date of Patent: Nov. 15, 1994

[54] ANTIMICROBIAL MATERIAL FOR BREEDING OR KEEPING FISH AND PROCESS FOR PRODUCING THE SAME

[76] Inventor: Etsuko Sugo, Gunma, Japan

[21] Appl. No.: 693,544

[22] Filed: Apr. 30, 1991

[30] Foreign Application Priority Data

Mar. 18, 1991 [JP] Japan ................... 3-052252

[51] Int. Cl.⁵ ............ A61K 31/74; A61K 31/75; A61K 31/745; A01K 63/00
[52] U.S. Cl. ................ 424/78.17; 424/78.28; 424/78.29; 424/78.27
[58] Field of Search .......... 424/78, 78.17, 78.18, 424/78.26, 78.27, 78.28, 78.29; 119/5

[56] References Cited

U.S. PATENT DOCUMENTS

| | | | |
|---|---|---|---|
| 4,076,619 | 2/1978 | Howery | 119/5 |
| 4,413,999 | 11/1983 | Linder et al. | 424/78.17 |
| 4,617,326 | 10/1986 | Björnberg et al. | 424/78 |
| 4,966,872 | 10/1990 | Horowitz et al. | 252/175 |

FOREIGN PATENT DOCUMENTS

| | | |
|---|---|---|
| 10042075 | 5/1981 | European Pat. Off. . |
| 10117478 | 2/1984 | European Pat. Off. . |
| 1282390 | 11/1989 | Japan . |
| 901039 | 10/1958 | United Kingdom . |
| 2009762 | 12/1978 | United Kingdom . |

OTHER PUBLICATIONS

J. C. Winters Journal of Society of the Cosmetic Chemists pp. 256–267.

Primary Examiner—Thurman K. Page
Assistant Examiner—Peter F. Kulkosky
Attorney, Agent, or Firm—Fish & Richardson

[57] ABSTRACT

An antimicrobial material for fish breeding or keeping comprising a formed article of a pulp and/or polyolefin base material and a process for producing the same are disclosed, in which said formed article contains a functional group having a function of removing harmful ions combined with an antimicrobial activity. The material is produced by graft polymerizing a reactive monomer on a formed article of a pulp and/or polyolefin base material and introducing a functional group having a function of removing harmful ions combined with an antimicrobial activity into the grafted chain of the graft polymer. By the use of the material, fish keeping including transportation can be carried out stably and efficiently.

4 Claims, No Drawings

5,364,638

ANTIMICROBIAL MATERIAL FOR BREEDING OR KEEPING FISH AND PROCESS FOR PRODUCING THE SAME

FIELD OF THE INVENTION

This invention relates to a material useful in transportation and breeding or keeping food fish or aquarium fish and a process for producing the same. More particularly, it relates to an antimicrobial material with which food fish can be kept alive for an extended period of time and a process for producing the same.

BACKGROUND OF THE INVENTION

With recent more variety in eating habit, there has been an increasing demand for transportation of food fish alive. Up to the present time, low-temperature transportation of living fish in a dormant condition is widely spread. However, this method involves disadvantages of a low rate of survival after transferring the fish to an aquarium and a large consumption of electric power. On the other hand, in a transportation method of using a water tank in which fish are maintained in usual conditions, a large amount of oxygen is required and a density of fish in the tank is low. The density of fish during transportation from a fishing ground to a fishing port and during storage in a fishing port before delivery and rate of survival are directly linked with cost and are therefore important factors of transportation of living fish.

If a fish density is increased, the ammonia concentration in the water tank increases and, eventually, the fish perish from an increased concentration of a nitrite ion, due to a decomposition product of ammonia. To avoid this, a combined filtration method is employed, in which ammonia in a water tank is adsorbed onto activated carbon, coral sand, etc. and bacteria capable of degrading harmful substances are allowed to proliferate, but the problems have not yet come to satisfactory solutions.

Further, as the fish density increases, the rate of disease during fish keeping tends to be increased. For example, infection with infectious diseases, such as oodiniosis, trichodimiasis, lymphocystis disease, white spot disease, and tail rot, has arose a serious problem.

Various problems remaining unsolved as mentioned above, reliability in breeding, keeping, and transportation of fish is still low, and it has been demanded in various fields to find a solution as soon as possible.

SUMMARY OF THE INVENTION

Accordingly, an object of the present invention is to provide a material with which transportation and breeding or keeping of fish can be carried out stably and efficiently and a process for producing such a material.

As a result of extensive and intensive investigations, the inventors have found that the above object of the present invention can be accomplished by an antimicrobial material for breeding or keeping of fish comprising a formed article of a pulp and/or polyolefin base material, wherein said formed article contains a functional group having a function of removing harmful ions combined with an antimicrobial activity.

The antimicrobial material of the invention can be produced by a process comprising graft polymerizing a reactive monomer on a formed article of a pulp and/or polyolefin base material and introducing a functional group having a function of removing harmful ions combined with an antimicrobial function into the graft polymer.

Conventional ion exchange techniques were incapable of selectively removing an ammonia ion or a nitrite ion in the seawater because of existence of large quantities of sodium and chloride ions. On the contrary, since the antimicrobial material according to the present invention has a functional group possessing both cationic and anionic properties which are mutually offset, it is capable of selectively absorbing and removing harmful ions, e.g., an ammonia ion and a nitrite ion, without adsorbing a sodium ion or a chloride ion.

DETAILED DESCRIPTION OF THE INVENTION

The base material which can be used in the present invention is pulp and/or a polyolefin including paper pulp, regenerated paper, polyethylene, and polypropylene. The base material to be used can be selected appropriately from among them according to the end use. Acrylic fibers may also be used as a base material because the cyano group present in acrylic fibers can be converted to a carboxyl group or an amidoxime group by making use of, e.g., hydrolysis. However, from the standpoint of strength and performance properties, pulp and/or polyolefin base materials are preferred to acrylic fibers. These base materials preferably have a fibrous form for assuring a wider surface area, which leads to an increased rate of adsorption of harmful substances, and more ease of forming into any desired shape. The fibers preferably have a fiber diameter of from 1 to 50 μm. With the diameter being within the preferred range, graft polymerization takes place uniformly over the cross-section of fibers.

A formed article comprising the base material has an aggregate form, such as mat, non-woven fabric, or a mass of spheres or flakes. For use in transportation or keeping of fish for a relatively short period of time, spherical or flaky formed articles are preferred. In this case, the effect of removing harmful substances and antimicrobial activity can be exhibited simply by placing such spherical or flaky material in a water tank or an aquarium. For use in high-density transportation or long-term keeping of fish, non-woven fabric is effectively employed as a by-pass filter which serves not only as an adsorbent for harmful substances, but also as a filter for collecting any suspended matter and as a bed for proliferation of useful bacteria. Besides, these formed articles exhibit antimicrobial activity to prevent infectious diseases, such as oodiniosis, trichodimiasis, lymphocystis disease, white spot disease, and tail rot. In application to small fish, the spherical or flaky formed article is put in a polyethylene bag in which fish are kept, and oxygen is introduced in an amount dependent on fish density, followed by closing. In this case, the fish in the bag stand transportation and keeping for about 2 weeks while being protected from infection.

A reactive monomer is graft polymerized on the formed article. Reactive monomers which can be used in the present invention preferably include vinyl monomers. Specific examples of suitable reactive monomers include vinyl monomers containing a glycidyl group, e.g., glycidyl methacrylate, glycidyl acrylate, glycidyl methylitaconate, ethyl glycidyl maleate, and glycidyl vinyl sulfonate; and vinyl monomers containing a cyano group, e.g., acrylonitrile, vinylidene cyanide, crotononitrile, methacrylonitrile, chloroacrylonitrile, 2-cyanoethyl methacrylate, and 2-cyanoethyl acrylate.

Graft polymerization of the reactive monomer to the formed article can be carried out, for example, by polymerization in the presence of a polymerization initiator, thermal polymerization, irradiation-induced polymerization using ionizing radiation, e.g., α-rays, β-rays, γ-rays, accelerated electron rays. X-rays, and ultraviolet rays. Polymerization induced by γ-rays or accelerated electron rays is recommended for practical use.

The amount of a reactive monomer polymerized on the formed article is expressed in terms of grafting rate (%) obtained from equation:

$$\text{Grafting Rate} = \frac{\text{Weight after grafting} - \text{Weight before grafting}}{\text{Weight before grafting}} \times 100$$

In the present invention, a grafting rate preferably ranges from 10 to 150%. If the grafting rate is out of this range, performance properties characteristic of the base material tend to be impaired.

Modes of graft polymerization of a reactive monomer to a formed article are divided into liquid phase polymerization in which a formed articles is directly reacted with a liquid reactive monomer and gaseous phase polymerization in which a formed article is brought into contact with vapor or gas of a reactive monomer. Either of these polymerization modes can be chosen in the present invention according to the end use or purpose.

The functional group having a function of removal of harmful ions combined with an antimicrobial activity has a structure in which an amino group or an imino group is combined with a carboxyl group or an oxime group. More specifically, the functional group having the combined functions is selected from the group consisting of an amidoxime group, an imidodixime group, a monoaminomonocarboxyl group, a monoaminodicarboxyl group, and a diaminodicarboxyl group. The functional group is introduced into a grafted chain of a graft polymer.

Introduction of such a functional group to a formed article can be carried out by immersing the formed article to which a reactive monomer has been grafted in a methanol-water solution of hydroxylamine, glycine, phenylalanine, alanine, tryptophane, histidine, valine, leucine, serine, aspartic acid, or glutamic acid. Through the immersion, the above substance is addition-bonded to the grafted chain of the grafted polymer to impart desired combined functions to the graft polymer. The content of the functional group in the final product preferably ranges from 0.5 to 8 mmol per gram. As long as the functional group content falling within this range, the final product shows hydrophilic properties without impairing the characteristics of the base material.

It has not yet been made clear why and how the above-described functional group exhibits antimicrobial activity. It is a fact, anyway, that each of amino, imino, carboxyl, and oxime groups shows substantially no antimicrobial activity when used alone. That is, it is not until an amino group or an imino group is combined with a carboxyl group or an oxime group that such noticeable antimicrobial effects are exerted beyond comparison with conventional antimicrobial materials as demonstrated in the Examples hereinafter described. Thus, the antimicrobial material according to the present invention brings about a great improvement in the art.

The present invention is now illustrated in greater detail with reference to Examples, but it should be understood that the present invention is not deemed to be limited thereto. All the percents are by weight unless otherwise specified.

EXAMPLE 1

Polypropylene fibers having a fiber diameter of 20 μm were formed into spheres having an average diameter of 5 mm. The spheres were irradiated with accelerated electron rays at a dose of 10 Mrad in a nitrogen atmosphere by means of an electron ray accelerator. Then, the irradiated formed article was brought into contact with an oxygen-free acrylonitrile for 2 hours to conduct graft polymerization, followed by thoroughly washing with dimethylformamide to obtain a graft polymer having a grafting rate of 90%. The resulting polymer was immersed in a 30% methanol-water solution of hydroxylamine at 80° C. for 5 hours to add hydroxylamine to the cyano group in the grafted chain and thoroughly washed with warm water. There was obtained an antimicrobial material for fish keeping containing in the grafted chain thereof 6.5 mmol of a combination of an amino group and an oxime group per gram.

Ten grams of the resulting antimicrobial material was put in a polyethylene bag of 30 cm×40 cm, and five gold-fishes of middle size were put therein together with 2 l of water. The bag was filled with oxygen gas and then closed. Even after keeping the fishes for 4 weeks at 20° C., no turbidity of water was observed, and all the goldfishes were found healthy and uninfected with dermatitis, tail rot disease or a like infectious disease. The dissolved ammonia ion concentration and dissolved nitrite ion concentration after 4 weeks were 0.1 ppm and 0.2 ppm, respectively, demonstrating capability of the antimicrobial material in adsorption and removal of harmful ions.

For comparison, the same test was conducted without using the antimicrobial material. After 1 week's keeping, the water became opaque, and almost all of the goldfishes died.

It was thus proved from these results that the antimicrobial material of the present invention has a harmful ion adsorbing function and an antimicrobial activity, producing remarkable effects in keeping living fish in a closed container. Use of the antimicrobial material effects a significant improvement in the field of fish breeding and fish selling, making it feasible to transport living fish over a long distance and also making it possible for fish dealers having no special fish keeping equipment to make a bulk sale at their own store.

EXAMPLE 2

Polyethylene fiber having a fiber diameter of 25 μm were formed into non-woven cloth having a basis weight of 150 g/m². The non-woven cloth was irradiated with accelerated electron rays in a nitrogen atmosphere at 10 Mrad at an accelerated voltage of 2 MeV and an electron beam current of 1 mA by means of an electron ray accelerator and then brought into contact with an oxygen-free glycidyl methacrylate at 40° C. for 2 hours to conduct graft polymerization to a grafting rate of 150%. The resulting graft polymer was immersed in a 5% propanol-water solution of glycine to which NaOH had been added at 80° C. for 5 hours to add glycine to the glycidyl group. There was obtained an antimicrobial material containing 2.0 mmol/g of a combination of an amino group and a carboxyl group bonded to the grafted chain thereof.

A piece of 40 cm² was cut out of the resulting antimicrobial material and fixed to a filter of a 50 l-volume aquarium. Forty liters of fresh artificial seawater was put in the aquarium, and 10 cobalt damselfishes were kept therein while bubbling oxygen therethrough. After one day's keeping, the dissolved ammonia ion concentration and dissolved nitrite ion concentration were found to be 0.1 ppm and 0.05 ppm, respectively, and the seawater had a pH of 7.7. After one week, the dissolved ammonia ion concentration and dissolved nitrite ion concentration were 0.1 ppm and 0.1 ppm, respectively, and the seawater had a pH of 7.5. Even after 2 weeks, the concentrations of dissolved ions were stable, and all the fishes were found healthy without bearing any infectious disease, such as oodiniosis, trichodimiasis, lymphocystis disease, white spot disease, and tail rot. The similar results were obtained when the same test was performed, except for replacing the fresh artificial seawater with spend seawater and coral sand.

For comparison, the test was performed in the same manner, except for using a commercially available set for keeping tropical fish without using the antimicrobial material. Fresh artificial seawater was used immediately after preparation from tap water. After 1 week, the ratio of fishes which were alive an uninfected (healthy) was not more than 50%.

From these results, the antimicrobial material of the present invention was proved excellent in adsorption and removal of harmful ions and antimicrobial properties in keeping saltwater fish as well.

EXAMPLE 3

Regenerated paper flakes having an average particle size of 5 mm were immersed in the same volume of a glycidyl acrylate solution for 10 minutes. After removing excess liquid, the impregnated flakes were put in an irradiation chamber. The chamber was rendered oxygen-free, and cobalt 60 γ-rays were irradiated on the flakes over 1 hour at an absorption dose of 1 Mrad to conduct graft polymerization. The graft polymer was washed with dimethylformamide and then immersed in a 3% phenylalanine aqueous solution (pH=13) at 80° C. for 5 hours to add phenylalanine to the glycidyl group. There was produced an antimicrobial material containing 1.5 mmol/g of a combination of an amino group and a carboxyl group bonded to the grafted chain thereof.

In a 50 l-volume aquarium having no filtration means was put 50 g of the resulting antimicrobial material, and 40 l of fresh artificial seawater was charged therein to make the flakes float. Ten saltwater fishes of several kinds were kept in the aquarium while bubbling oxygen therethrough. After one week, the dissolved ammonia ion concentration and dissolved nitrite ion concentration were found to be 0.1 ppm and 0.1 ppm, respectively, and the seawater had a pH of 7.5. All the fishes were found healthy without suffering from any infectious disease.

From these results, it can be seen that use of the antimicrobial material of the present invention precludes the necessity of equipping a water tank for transportation of saltwater fish with a filtration means, thus establishing rationalization and stabilization of fish transportation.

While the invention has been described in detail and with reference to specific embodiments thereof, it will be apparent to one skilled in the art that various changes and modifications can be made therein without departing from the spirit and scope thereof.

What is claimed is:

1. An antimicrobial fish breeding material which comprises a formed article of a pulp and/or polyolefin base material, bonded on the surface thereof with graft polymerized chains having at least one functional group on said chains, said functional group having a function of removing harmful ions also having antimicrobial activity, wherein said functional group is selected from the group consisting of a monaminomonocarboxyl group, a monoaminodicarboxyl group, and a diaminodicarboxyl group, and is present in an amount of from 0.5 to 8 mmol per gram of said antimicrobial fish breeding material wherein said functional group is formed by after treatment reaction of reactive groups on said grafted chains with hydroxylamine, glycine, phenylalanine, alanine, tryptophane, histidine, valine, leucine, serine, aspartic acid or glutamic acid in a methanol-water solution.

2. An antimicrobial fish breeding material as claimed in claim 1 wherein said formed article is selected from the group consisting of paper pulp, regenerated paper, polyethylene and polypropylene.

3. An antimicrobial fish breeding material as claimed in claim 1 wherein said base material consists of fibers having a fiber diameter of from 1 to 50 μm.

4. A process for producing an antimicrobial fish breeding material of claim 1 which comprises the steps of:

graft polymerizing vinyl monomers having a glycidyl or cyano group onto the surface of a formed article of a pulp and/or polyolefin base material, and contacting the formed article with hydroxylamine, glycine, phenylalanine, alanine, tryptophane, histidine, valine, leucine, serine, aspartic acid or glutamic acid.

* * * * *